(12) United States Patent
Cook et al.

(10) Patent No.: US 9,035,077 B2
(45) Date of Patent: May 19, 2015

(54) TOTAL SYNTHESIS OF ARTEMISININ

(75) Inventors: Silas Cook, Bloomington, IN (US); Chun-Yin Zhu, Bloomington, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 14/114,748

(22) PCT Filed: May 10, 2012

(86) PCT No.: PCT/US2012/037214
§ 371 (c)(1),
(2), (4) Date: Jan. 20, 2014

(87) PCT Pub. No.: WO2012/154906
PCT Pub. Date: Nov. 15, 2012

(65) Prior Publication Data
US 2014/0135507 A1    May 15, 2014

Related U.S. Application Data

(60) Provisional application No. 61/484,317, filed on May 10, 2011.

(51) Int. Cl.
*C07D 493/16* (2006.01)
*C07D 493/18* (2006.01)

(52) U.S. Cl.
CPC .................................... *C07D 493/18* (2013.01)

(58) Field of Classification Search
USPC ........................................................ 549/348
See application file for complete search history.

(56) References Cited

U.S. PATENT DOCUMENTS

2006/0270863 A1   11/2006   Reiling et al.

OTHER PUBLICATIONS

Oh et al., "A Short Synthesis of 6,9-Desmethyldeoxoartemisinin and Its Isomer," Bull. Korean Chem. Soc. vol. 17, No. 7, pp. 581-582 (1996).
Posner et al., "Orally Active, Water-Soluble Antimalarial 3-Aryltrioxanes: Short Synthesis and Preclinical Efficacy Testing in Rodents," J. Med. Chem. vol. 45, pp. 3824-3828 (2002).
Binns et al., "An unsuccessful approach to the framework of the antimalarial, arteether," Tetrahedron Letters, vol. 30, No. 9, pp. 1125-1128 (1989).
Du Feu et al., "Experiments on the Synthesis of Substances related to the Sterols. Part XIV. A Simple Synthesis of Certain Octadones and Ketotetrahydrohydrindenes which may be of Angle-methyl-substituted Type. A Theory of hte Biogenesis of the Sterols," J. Chem. Soc. pp. 53-60 (1937).

(Continued)

Primary Examiner — Bruck Kifle
(74) Attorney, Agent, or Firm — Klintworth & Rozenblat IP LLC

(57) ABSTRACT

The present invention provides a method for manufacturing artemisinin and its congeners from cyclohexenone as a starting material.

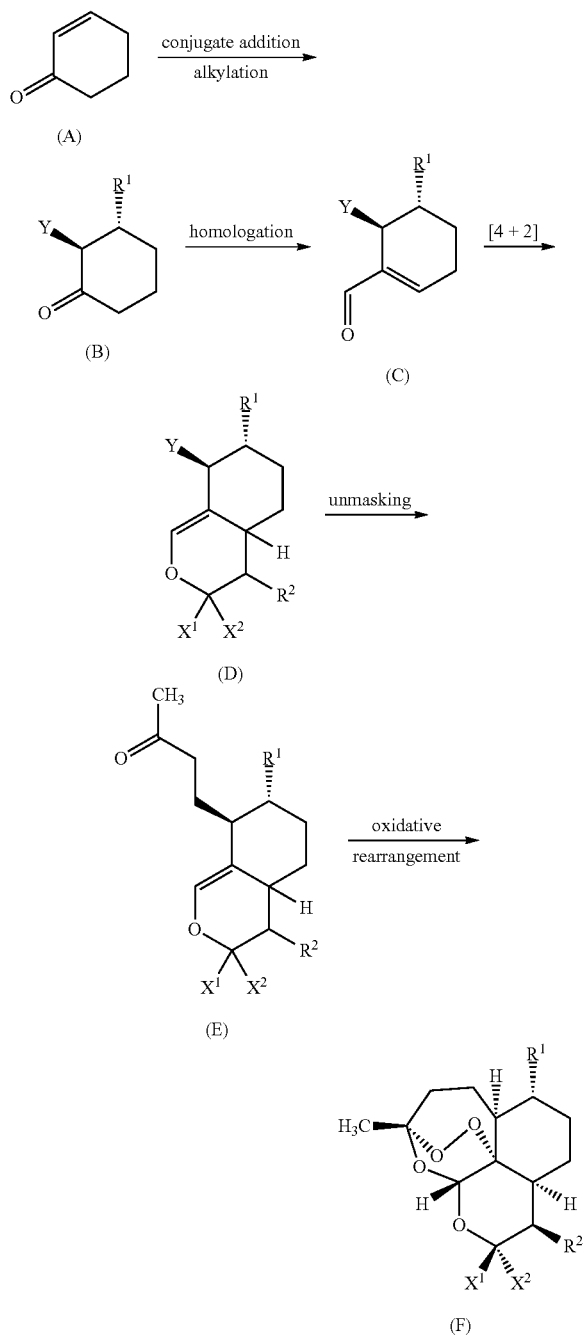

20 Claims, 2 Drawing Sheets

(56) References Cited

OTHER PUBLICATIONS

Theobald, "Sesquiterpenoids—VI, The chemistry of some compounds in the 14-Noreudesmane Series," Tetrahedron 1966, vol. 22, pp. 2869-2875 (1966).
Halsall et al. "Studies in th synthesis of terpenes. Part VIII.* The absolute configurations of elemol," J. Chem. Soc. 1029-1037 (1964).
Julia, "No. 162. Emploi du dichloro-1,2-butene 2 pour la snthese de quelquies cetones derivees du bicyclo-(1,3,3,) nonene et de l'hexahydro-napthalene," Bull. Soc. Chim. Fr. vol. 5, pp. 780-789 (1954) (no translation).
Stork et al. "A total synthesis of 11-oxygenated steroids," J. Am. Chem. Soc. vol. 78, 501-2 (1956).
Stork et al. "A general synthesis of 4-isoxazolecarboxylic acids," J. Am. Chem. Soc. vol. 89, 5461-5462 (1967).
Stork et al. "A general synthesis of esters of acryloyl acetic acid and their homologs," Tetrahedron Letters No. 27, pp. 2755-2758 (1972).
Wenkert, J. Am. Chem. Soc. 1964, 86, 2038.
Stork et al. "Vinylsilanes as Carbonyl Precursors. Use in Annelation Reactions," J. Am. Chem. Soc. vol. 96, 3682-3684 (1974).
Stotter et al. "Gamma-Halotiglates. A simple, efficient position-specific annelation of unsymmetrically substituted cyclohexanones," J. Am. Chem. Soc., vol. 96, pp. 6524-6526 (1974).
Stork et al. alpha-Silylated vinyl ketones. A new class of reagents for the annelation of ketones J. Am. Chem. Soc. vol. 95, 6152-6153 (1973).
Boeckman, Conjugate addition-annelation. A highly regiospecific and stereospecific synthesis of polycyclic ketones. J. Am. Chem. Soc. vol. 95, pp. 6867-6869 (1973).
World Malaria Report. 248 (World Health Organization, 2011).
Chang et al., "Engineering *Escherichia coli* for production of functionalized terpenoids using plan P450s," Nat. Chem. Biol. vol. 3, pp. 274-277 (2007).
Ro et al., "Production of the antimalarial drug precursor artemisinic acid in engineered yeast," Nature vol. 440, pp. 940-943 (2006).
Graham et al., "The generic map of *Artemisia annua* L. identifies loci affecting yield of the antimalarial drug artemisinin," Science vol. 327, pp. 328-331 (2010).
Wender et al., "Function-oriented synthesis, step economy, and drug design," Acc. Chem. Res. vol. 41, pp. 40-49 (2008).
Liu et al., "Structure and reaction of arteannuin," Hua. Xue. 37, 129-143 (1979).
Zhou et al. "Total Synthesis of the Antimalarial Sesquiterpene Peroxide Qinghaosu and Yingzhaosu A," Acc. Chem. Res. vol. 27, pp. 211-216 (1994).
Schmid et al., "Total Synthesis of Qinghaosu," J. Am. Chem. Soc., vol. 105, pp. 624-625 (1983).
Xu et al., "Total Synthesis of Arteannuin and Deoxyarteannuin," Tetrahedron vol. 42, pp. 819-828 (1986).
Avery et al., "The Total Synthesis of (+)-Artemisinin and (+)-9-Desmethylartemisinin," Tetrahedron Lett. vol. 28, pp. 4629-4632 (1987).
Ravindranathan et al., "Stereoselective synthesis of artemisinin," Tetrahedron Letters, vol. 31, pp. 755-758 (1990).
Avery et al., "Stereoselective Total Synthesis of (+)-Artemisinin, the Antimalarial Constituent of Artemisia-Annua L," J. Am. Chem. Soc., vol. 114, 974-979 (1992).
Liu et al., "A Total Synthesis of the Antimalarial Natural Product(+)-Qinghaosu," Tetrahedron Letters, vol. 34, pp. 4435-4438 (1993).
Constantino et al., "A novel asymmetric total synthesis of (+)-artemisinin," Synthetic Commun., vol. 26, pp. 321-329 (1996).
Liu et al., "Total synthesis of (−)-qinghaosu IV (artemisinin D, arteannuin D)," Heterocycles, vol. 42, pp. 493-497 (1996).
Yadav et al., "A concise stereoselective total synthesis of (+)-artemisinin, "Tetrahedron, vol. 66, 2005-2009 (2010).
White, "Qinghaosu (artemisinin): the price of success," Science, vol. 320, pp. 330-334 (2008).
Martin et al., "Engineering a mevalonate pathway in *Escherichia coli* for production of terpenoids," Nat. Biotechnol., vol. 21, pp. 796-802 (2003).
Tsuruta et al., "High-level production of amorpha-4,11-diene, a precursor of the antimalarial agent artemisinin, in *Escherichia coli*," Plos One, vol. 3, e4489 (12 pages) (2009).
Westfall et al., "Production of amorphadiene in yeast, and its conversion to dihydroartemisinic acid, precursor to the antimalarial agent artemisinin," Proc. Natl. Acad. Sci. U.S.A., vol. 109, E111-118 (2012).
Van Noorden, "Demand for maleria drug soars," Nature, vol. 466, pp. 672-673 (2010).
Stork et al., "The mechanism of the Isoxazole annelation," J. Am. Chem Soc., vol. 89, pp. 5463-5464 (1967).
Singletary et al., "A succinct method for preparing the Stork-Jung vinylsilane Robinson annulation reagent," J. Org. Chem., vol. 70, pp. 739-741 (2005).
Jarugumilli et al., "Re-Evaluating the Nucleophilicity of Zinc Enolates in Alkylation Reactions." Eur. J. Org. Chem., vol. 2012, 1712-1715 (2012).
Shapiro et al., Tosylhydrazones and Alkyllithium Reagants—More on Regiospecificity of Reaction and Trapping of 3 Intermediates, Tetrahedron Letters, No. 22 + 23, 1811-1814 (1975).
Aben et al., "High Pressure-Promoted Cycloadditions of Ketene Acetals and Alpha,Beta-Unsatured Aldehydes and Ketones," Tetrahedron Letters, vol. 26, pp. 1889-1892 (1985).
Hoppe et al., "An Approach to Bufadienolides from Deoxycholic-Acid. Reactions of a Steroidal Alpha,Beta-Unsatured Aldehyde with Some Ortho-Silylated Ketene Acetals," Tetrahedron, vol. 45, pp. 3695-3710 (1989).
Taber, "A simple synthesis of 2-alkylcyclohexenones," J. Org. Chem., vol. 41, pp. 2649-2650 (1976).
International Search Report and Written Opinion of the International Search Authority mailed Jul. 2, 2012 for International Application No. PCT/US2012/037214—8 pages.
Boger, D. L. 1999. Modern Organic Synthesis (Lecture Notes) [TSRI Press, LoJolla, CA (USA)], pp. 270-273.
Nagel, A. A. 2001. "2-Methyl-6-vinylpyridine," e-EROS Encyclopedia of Reagents for Organic Synthesis.
Danishefsky, S. Cain, P. and Nagel A. 1975. "Bis Annelations via 6-Methyl-2-vinylpyridine. An Efficient Synthesis of dl-D-Homoestrone" J. Am. Chem. Soc. 97:380-387.
Weichert, A. and Hoffmann, H.M.R. 1991. "Synthesis and Reactions of α-Methylene-β-keto Sulfones," J. Org. Chem. 56:4098-4112.
Colapret, J. A., Buonora, P. T. and Inomata, K. 2008. "Methyl Vinyl Ketone," e-EROS Encyclopedia of Reagents for Organic Synthesis.

TOTAL SYNTHESIS OF ARTEMISININ

CROSS-REFERENCE TO RELATED APPLICATIONS

The present application is the National Stage of International Application No. PCT/US12/37214, filed May 10, 2012, which claims the benefit of U.S. Provisional Patent Application No. 61/484,317 filed May 10, 2011. The content of the U.S. Provisional Patent Application is hereby incorporated by reference in its entirety.

BACKGROUND

Malaria infects over 200 million people each year with up to one million, mostly children, perishing from the infection [1]. Currently, the most effective treatment against malaria-causing *Plasmodium* parasites is artemisinin-based combination therapy (ACT). The key ingredient for the production of ACTs, artemisinin (1), is a natural product extracted on industrial scale from the sweet wormwood plant, *Artemisia annua*. Unfortunately, artemisinin is currently too expensive to meet the distribution needs of the world. Moreover, crop disruptions caused by natural disasters, poor planning and geopolitical events have led to shortages and price fluctuations. In the decade leading to 2012, there have been two primary approaches to combat these problems: using synthetic biology to produce a chemical precursor of artemisinin in microbes [2, 3], or breeding new varieties of *Artemisia annua* with improved growth and/or production traits [4]. While advances have been made in both areas, these strategies have yet to make a contribution to the world's artemisinin supply. Interestingly, the literature over the last decade reveals a disappointing lack of effort focused on discovering a de novo synthesis of 1 and its derivatives from inexpensive, readily available chemicals—a significantly more affordable and timely research proposition.

Soon after the initial report of the structure and anti-malarial activity of artemisinin (1), chemists began working towards a feasible chemical synthesis of the unprecedented endoperoxide-containing natural product [7]. This work culminated in several total syntheses of artemisinin (1) between 1979 and 1996 [6, 8-15]. While impressive from a chemical "proof-of-principle" perspective, these early syntheses have done little to address the supply problems of artemisinin (1) because of the high costs inherent to long reaction sequences, excessive protecting group schemes and expensive terpene-based starting materials (FIG. 1). Even modern syntheses of artemisinin (1) cannot compete on price with isolation from natural sources [16]. These problems have driven the perception that a laboratory synthesis of artemisinin (1) is untenable [17].

FIGURES

DEFINITIONS

Figure 1:
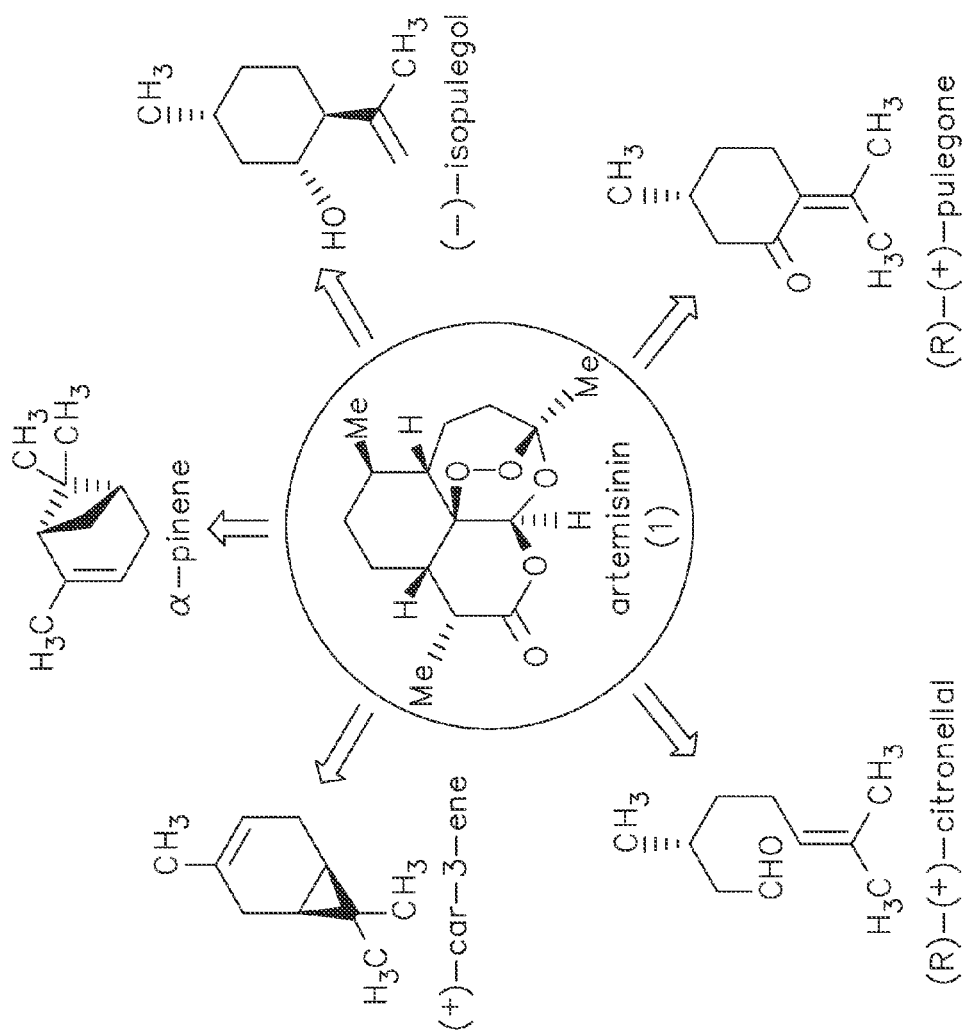
FIG. 1 illustrates the structure of artemisinin (1) and the various terpene starting materials used in previous total syntheses.

As used herein, the terms "a" and "an" include singular as well as plural references unless the context clearly dictates otherwise.

As used herein, the term "MVK equivalent" refers to a reactant used to functionalize a molecule in such a way as to allow future access to a moiety having formula —$CH_2CH_2$—$C(O)$—$CH_3$. As methyl vinyl ketone (MVK) can be difficult to employ due to its tendency to polymerize, MVK equivalents are usually employed as surrogates for MVK itself. Typically, a molecule is first reacted with a MVK equivalent to yield an intermediate bearing a moiety of formula Y, where Y is a "masked MVK moiety." The masked MVK moiety is then "unmasked," i.e. subjected is to further transformation(s) to transform it into moiety —$CH_2CH_2$—$C(O)$—$CH_3$. The masked MVK moiety may be unmasked right after the reaction with the MVK equivalent or at a later stage in the synthesis of a desired product. Example MVK equivalents include crotyl bromide and the molecules depicted in Table 1.

As used herein, the term "alkyl" refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "cycloalkyl" refers to a monocyclic, bicyclic, tricyclic, spirocyclic, or polycyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups of the present invention may contain one or two alkylene bridges of 1, 2, 3, or 4 carbon atoms, wherein each bridge links two non-adjacent atoms within the groups. Examples of such bridged cycloalkyls include, but are not limited to, bicyclo[3.1.1]heptyl (including but not limited thereto, bicyclo[3.1.1]hept-2-yl), bicyclo[2.2.1]heptyl, bicyclo[3.1.1]heptyl, bicyclo[2.2.2]octyl, bicyclo[3.3.1]nonyl, adamantyl (tricyclo[3.3.1.13,7]decane), and noradamantyl (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups of the present invention can be appended to the parent molecular moiety through any substitutable carbon atom of the groups.

The term "heterocycle" or "heterocyclic," as used herein, refers to a monocyclic, bicyclic, tricyclic, or polycyclic ring system. Monocyclic ring systems are exemplified by any 3- or 4-membered ring containing a heteroatom independently selected from oxygen, nitrogen and sulfur; or a 5-, 6-, 7- or 8-membered ring containing one, two or three heteroatoms wherein the heteroatoms are independently members selected from nitrogen, oxygen and sulfur. The 5-membered ring has from 0-2 double bonds and the 6-, 7-, and 8-membered rings have from 0-3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl(thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another heterocyclic monocyclic ring system. Bicyclic ring systems can also be bridged and are exemplified by any of the above monocyclic ring systems joined with a cycloalkyl group as defined herein, or another non-aromatic heterocyclic monocyclic ring system. Representative examples of bicyclic ring systems include but are not limited to, for example, benzimidazolyl, benzoazepine, benzothiazolyl, benzothienyl, benzoxazolyl, benzofuranyl, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1]nonane, octahydro-pyrrolo[3,4-c]pyrrole, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl, tetrahydroquinolinyl, and thiopyranopyridyl.

As used herein, the term "aryl," refers to a monocyclic-ring system or a polycyclic-ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

As used herein, the term "carboxyalkyl" refers to a carboxy group appended to the parent molecular moiety through an alkyl group as defined herein.

As used herein, the term "silyl ketene acetal" is a molecule bearing a moiety of formula —C=C(OSiR$^c_3$)(OR$^d$). Representative examples include molecules where the R$^c$ moieties are each an alkyl group, and R$^d$ is also an alkyl group.

SUMMARY OF THE INVENTION

In one aspect, a method for manufacturing molecules of Formula F is provided:

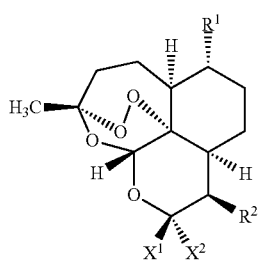

F the method comprising the steps of: forming a mixture by mixing ingredients comprising cyclohexenone, an alkylating agent, and an MVK equivalent, to form a first synthetic intermediate of Formula B:

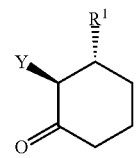

B wherein $R^1$ is an alkyl moiety and Y is a masked —CH$_2$CH$_2$C(O)CH$_3$ moiety; homologating the intermediate of Formula B to an aldehyde intermediate of Formula C:

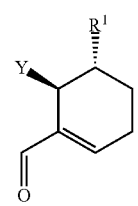

C forming a mixture by mixing ingredients comprising the intermediate of Formula C and a dienophile, to form an intermediate of Formula D:

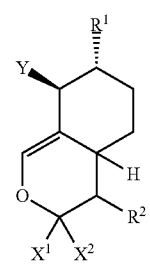

D wherein: $R^2$ is selected from the group consisting of —H, alkyl, cycloalkyl, heterocycle, and aryl, and at least one of $X_1$ and $X_2$ is selected from the group consisting of —H, —OH, —OCH$_3$, —OCH$_2$CH$_3$, —OSiR', —OR", and carbonyl oxygen, wherein R' is alkyl and R" is alkyl; converting moiety Y to a —CH$_2$CH$_2$C(O)CH$_3$ group, to form an intermediate of Formula E, and

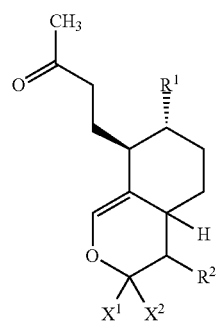

E forming a mixture by mixing ingredients comprising the intermediate of Formula E, hydrogen peroxide, and a metal catalyst.

In another aspect, a method for manufacturing artemisinin is provided, comprising the steps of: forming a mixture by mixing ingredients comprising cyclohexenone, a methylating agent, and crotyl bromide, to form a first synthetic intermediate of Formula 7:

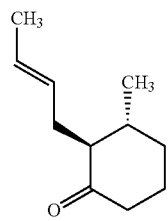

7 homologating the intermediate of Formula 7 to an aldehyde intermediate of Formula 5b:

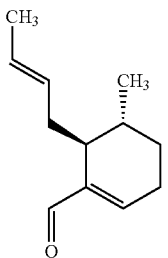

5b forming a mixture by mixing ingredients comprising the intermediate of Formula 5b and a compound of Formula 8, to form an intermediate of Formula 9:

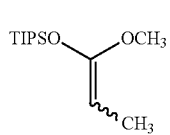

8

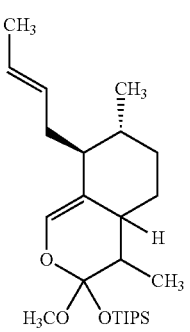

9 forming a mixture by mixing ingredients comprising the intermediate of Formula 9, hydrogen peroxide, and a palladium catalyst, to form an intermediate of Formula 10:

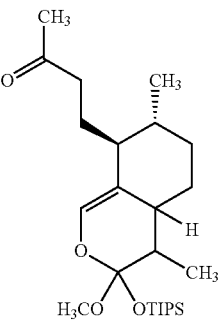

10 and forming a mixture by mixing ingredients comprising the intermediate of Formula 10, hydrogen peroxide, and a molybdenum catalyst.

In a further aspect, a method for manufacturing artemisinin is provided, comprising the steps of: forming a mixture by mixing ingredients comprising the compound of Formula 5b and the compound of Formula 8a, to form the intermediate of Formula 9a:

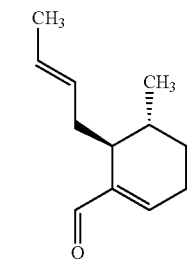

5b

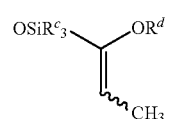

8a

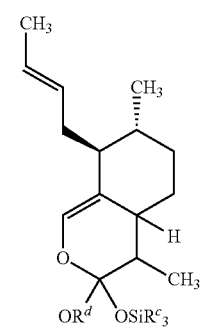

9a forming a mixture by mixing ingredients comprising the intermediate of Formula 9a, hydrogen peroxide, and a palladium catalyst, to form the intermediate of Formula 10a:

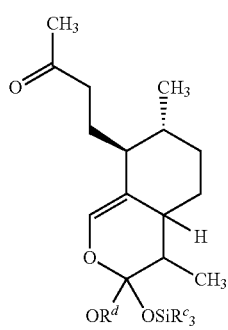

10a and forming a mixture by mixing ingredients comprising the intermediate of Formula 10a, hydrogen peroxide, and a catalyst comprising molybdenum, wherein $R^c$ is alkyl, and $R^d$ is alkyl.

DETAILED DESCRIPTION

The present application is based on the discovery of a novel, alternative approach to synthesizing artemisinin (1) and its congeners, such as compounds (2a-d). The synthesis described herein allows for the cost-effective preparation of artemisinin (1) by reducing production time and cost while increasing the availability of ACT, the most effective treatment against malaria.

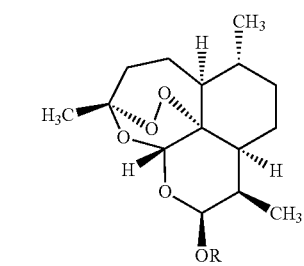

| | (2) |
|---|---|
| Artemether: R = —CH$_3$ | (2a) |
| Arteether: R = —CH$_2$CH$_3$ | (2b) |
| Artesunate: R = —C(O)(CH$_2$)$_2$CO$_2$Na | (2c) |
| Dihydroartemisinin: R = H | (2d) |

This approach provides a step-economical [5] method for the low-cost production of artemisinin (1) and its derivatives. In order to realize a strategy based on cheap, readily available chemical inputs, step economy, and overall efficiency, the use of protecting groups is minimized and cascade reactions are relied on to build in significant molecular complexity at each synthetic step.

In a first aspect, a synthetic method is provided as outlined below in Scheme 1:

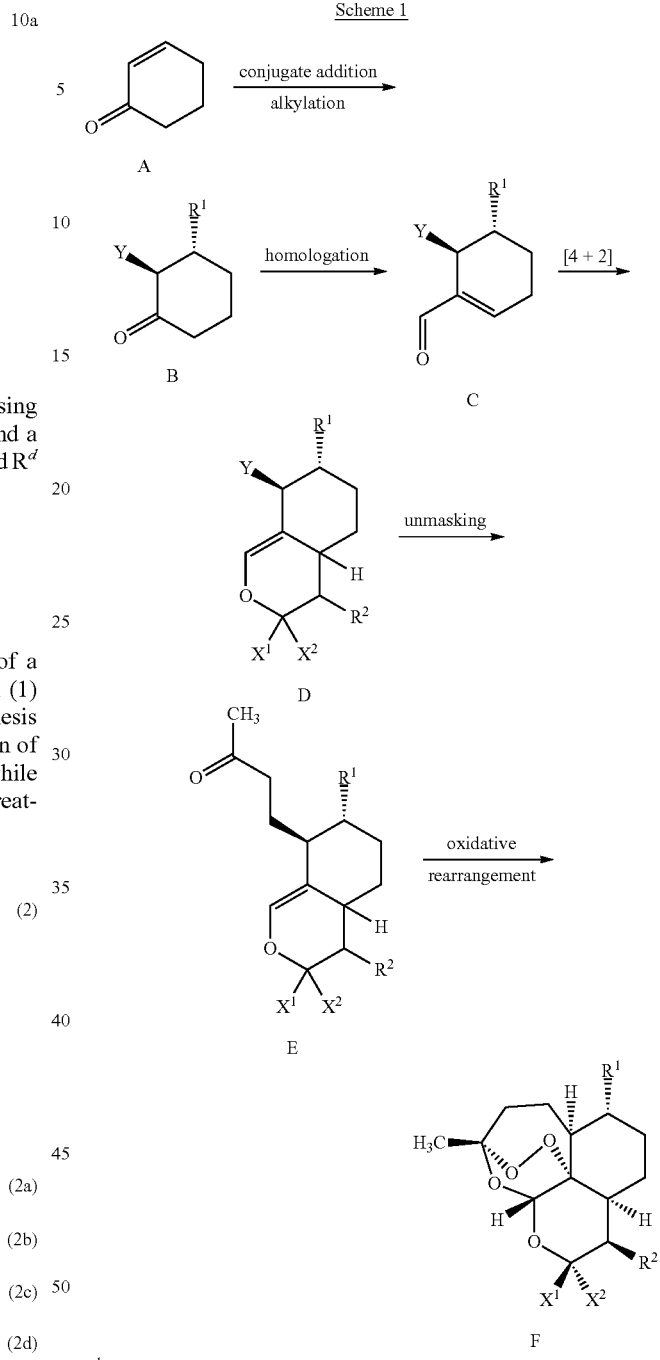

Scheme 1

$R^1$ = alkyl
$R^2$ = —H, —CH$_3$, alkyl, cycloalkyl, heterocycle, aryl
At least one of $X^1$ and $X^2$ = —H, —OH, —OMe, —OEt, —OSiR'$_3$ (where R' = alkyl) or any other alcohol-protecting group. Also, $X^1$ may be =O, with no $X^2$ present Y = masked —CH$_2$CH$_2$C(O)CH$_3$ Cyclohexenone A is alkylated and reacted with an MVK equivalent to yield a synthetic intermediate of Formula B. The alkylation can be carried out with an alkylating agent. Example alkylating agents include organometallic compounds such as organozinc compounds. For instance, the alkylating agent may be dimethylzinc (or diethylzinc) in a copper-catalyzed 1,4-addition to cyclohexenone. The alkylation may be carried out in the presence of a chiral ligand such as a chiral phosphoramidite. The MVK equivalent may be one of those listed in Table 1, such as the Stork-Jung vinyl silane [22] or crotyl bromide, or any other four-carbon unit capable of becoming a methyl ketone.

TABLE 1

| MVK Equivalent | Reference(s) Disclosing MVK Equivalent |
|---|---|
| ![structure] X = NR$_2$, N$^+$R$_3$, Cl | Robinson, *J. Chem. Soc.* 1937, 53. Theobald, *Tetrahedron* 1966, 22, 2869. Halsall *J. Chem. Soc.* 1964, 1029. |
| ![structure] Cl—/=\—Cl | Julia, *Bull. Soc. Chim. Fr.* 1954, 5, 780. |
| ![structure] I—/=\—OEt | Stork, *J. Am. Chem. Soc.* 1956, 78, 501 |
| ![structure] R-isoxazole-CH$_2$Cl | Stork, *J. Am. Chem. Soc.* 1967, 89, 5461 and 5463 |
| ![structure] CO$_2$CH$_3$ | Stork, *Tetrahedron Lett.* 1972, 2755. Wenkert, *J. Am. Chem. Soc.* 1964, 86 2038. |
| ![structure] I—/=\—SiMe$_3$ | Stork, *J. Am. Chem. Soc.* 1974, 96, 3682. |
| ![structure] I—/=\—CO$_2$tBu | Stotter, *J. Am. Chem. Soc.* 1974, 96, 6524. |
| ![structure] TMS-C(=O)-/=\ | Stork, *J. Am. Chem. Soc.* 1973, 95, 6152. Boeckman, *J. Am. Chem. Soc.* 1973, 95, 6867. |

Crotyl bromide is an advantageous MVK equivalent due to its low cost. The methylation and the reaction with crotyl bromide may be carried out as a one-pot conjugate addition/alkylation, which is believed to occur by a mechanism whereby the copper or zinc enolate formed by the conjugate addition is alkylated with an MVK equivalent such as crotyl bromide.

An intermediate of Formula B may also be obtained according to the procedure of Scheme 2 [29]:

Scheme 2

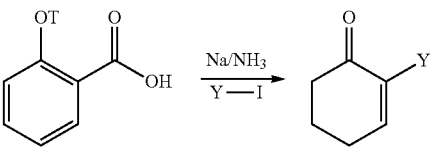

where T is an alkyl group, such as methyl, and —Y may be, for instance, —CH$_2$CH$_2$CH=CH$_2$. The product of Scheme 2 may then be alkylated, for example with an organozinc alkylating agent, to yield an intermediate of Formula B.

Next, intermediate B is homologated to the α,β-unsaturated aldehyde intermediate C. The homologation may be carried out through a one-step process, but higher yields have been achieved through a two-step Shapiro process. In the first step, intermediate B is reacted with p-toluenesulfonylhydrazide to obtain a p-toluenesulfonylhydrazone. The p-toluenesulfonylhydrazone is then reacted with a strong base, such as n-butyllithium (n-BuLi), and dimethylformamide, to yield C.

The Y moiety may then be "unmasked," that is converted to —CH$_2$CH$_2$C(O)CH$_3$. In instances where the Y moiety is a —CH$_2$CH=CHCH$_3$ or —CH$_2$CH$_2$CH=CH$_2$ group, the unmasking may be carried by an oxidation reaction. Alternatively, the unmasking may be carried out at a later stage in the synthesis, for example right prior to the synthetic step leading to the formation of the endoperoxide bridge moiety.

Intermediate C, which may bear the unmasked —CH$_2$CH$_2$C(O)CH$_3$ group instead of moiety Y, is then reacted with a dienophile in a [4+2] reaction yielding an intermediate of Formula D, where the nature of moieties $X_1$ and $X_2$ depends on the dienophile employed. For example, when the dienophile is a silyl ketene acetal, such as 8, the product D is an ortho ester, such as 9 (Scheme 3). A dienophile bearing a carbonyl group, such as propionyl chloride 12, will instead yield a lactone such as 13, where $X_1$ is a carbonyl oxygen and no $X_2$ is present (Scheme 3). In another example, the dienophile is a vinyl ether 14a-c that may be used to synthesize 2a-c via compounds 15a-c (Scheme 3).

The [4+2] reaction may be carried out in the presence of additional compounds, including: catalysts, for instance Lewis acids such as aluminum salts; bases, for example when required to generate dienophile enolates; and other compounds that may be used to promote and/or control [4+2]-type reactions (e.g., the Diels-Alder reaction). Among Lewis acids, dialkylaluminum chloride salts have been found to preferentially catalyze the formation of the desired products relative to other reactions.

Scheme 3

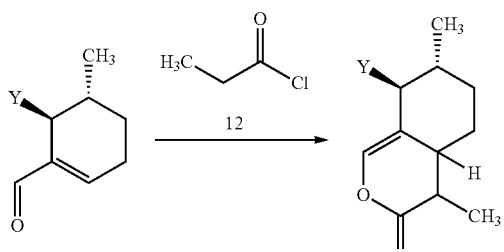

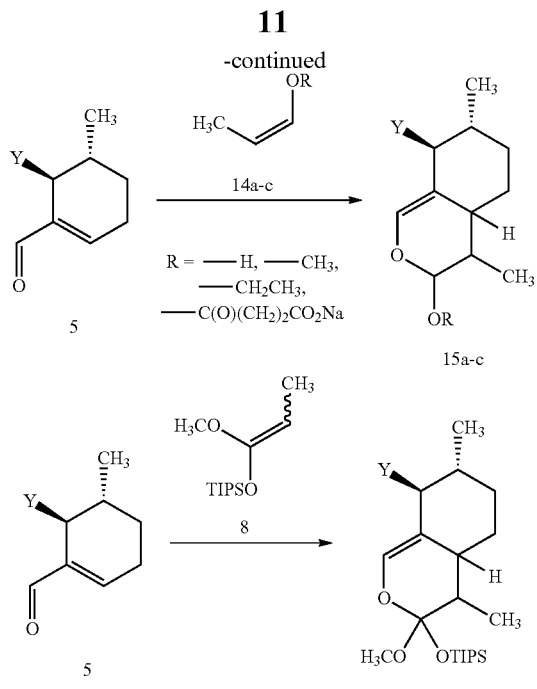

The Y moiety is now unmasked to —CH$_2$CH$_2$C(O)CH$_3$, if this conversion has not been carried out prior to the formation of D. The specific chemistry of the unmasking reaction(s) depends on the type of Y moiety present in D, and is therefore dependent on the MVK equivalent chosen in the above synthesis of B. As set for above, for instance, the unmasking may be carried out by subjecting D to an oxidation to yield an intermediate of Formula E.

This oxidation may be carried out with a peroxide oxidizer in the presence of a palladium catalyst. Example peroxide oxidizers include hydrogen peroxide (H$_2$O$_2$) and organic peroxides such as tert-butyl hydroperoxide (tBuOOH). Example palladium catalysts include palladium salts such as PdCl$_2$.

Then, E is subjected to an oxidative rearrangement to yield a product of Formula F. The oxidative rearrangement may be accomplished with singlet oxygen which may be generated in situ from hydrogen peroxide in the presence of a metal catalyst. The metal in the metal catalyst may be selected from lanthanum, cerium, molybdenum, calcium, tungsten, scandium, titanium, zirconium, vanadium, and combinations thereof. Example molybdenum catalysts include ammonium molybdate, ammonium heptamolybdate, molybdic acid, molybdic oxide, molybdenum trioxide, barium molybdate, calcium molybdate, iron molybdate, lead molybdate, potassium molybdate and strontium molybdate. In particular, ammonium molybdate ((NH$_4$)$_2$MoO$_4$) has been found to produce the highest yields of desired products.

Example 1

Figure 2:
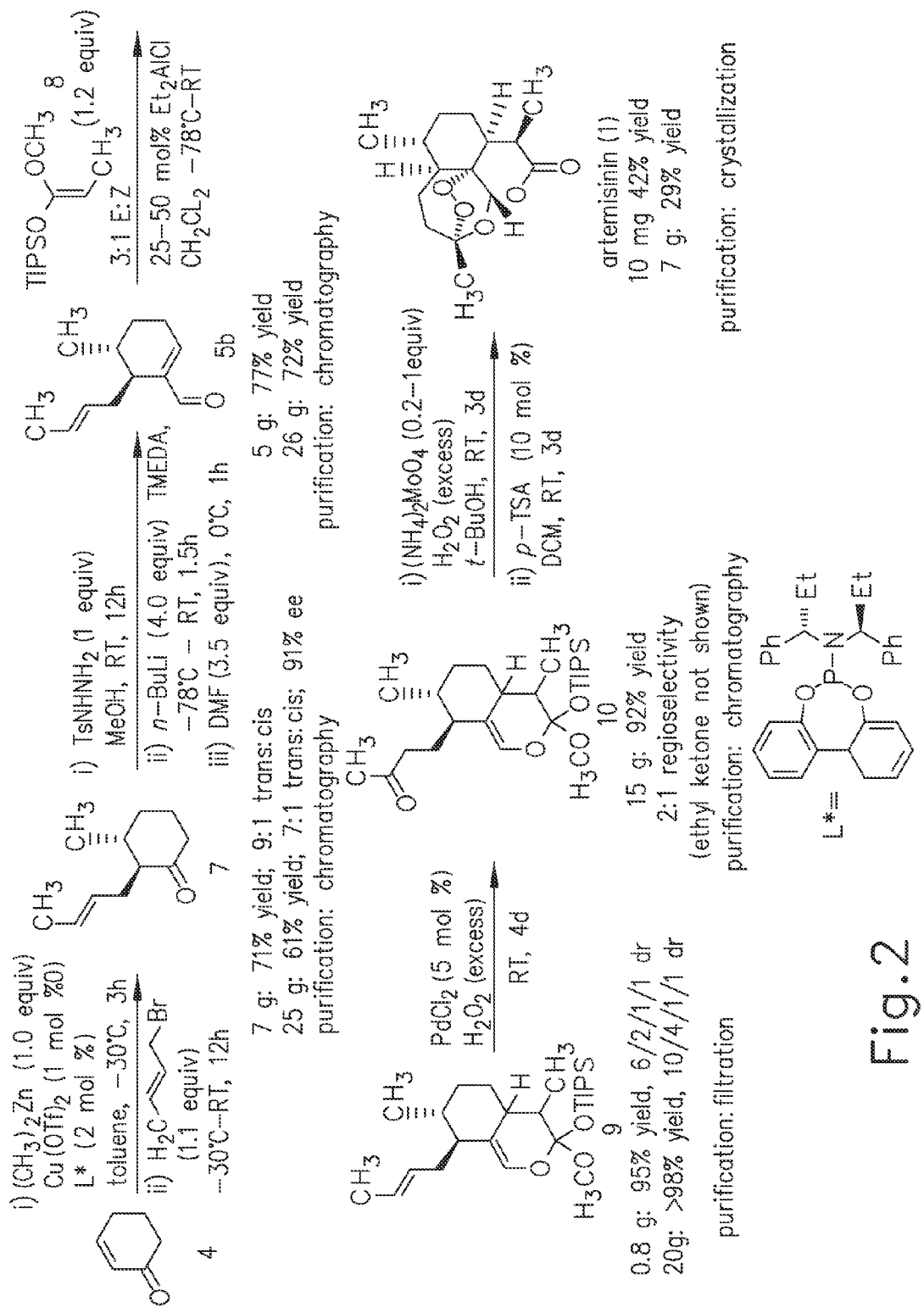
FIG. 2 illustrates a synthesis of (1).

As illustrated in FIG. 2, the example synthesis of artemisinin (1) began with the conversion of cyclohexenone 4 to ketone 7 in 61% yield (7:1 trans:cis, 91% enantiomeric eccess) via a one-pot conjugate addition/alkylation sequence [24] relying on crotyl bromide as a cost-effective MVK equivalent. The treatment of cyclohexanone 7 with p-toluenesulfonylhydrazide in methanol at room temperature provided the corresponding hydrazone. After replacing the solvent, exposure of the hydrazone to n-BuLi at low temperature provided a vinyl anion that was quenched with dimethylformamide [25]. This one-pot sequence resulted in the production of α,β-unsaturated aldehyde 5b in 72% overall yield.

A novel [4+2] reaction was developed for the installation of the six-membered lactone of artemisinin (1). An extensive investigation of acid catalysts revealed the ability of dialkylaluminum chloride salts to preferentially catalyze the formation of the [4+2] product relative to alternate pathways leading to Mukaiyama aldol or Michael products [26, 27]. In particular, it was found that the reaction of silyl ketene acetal 8 and 5b in the presence of dimethyl- or diethylaluminum chloride provides ortho ester 9 in ≥95% yield as a mixture of four diastereomers (10:4:1:1).

Extensive experimentation lead to the discovery that by stirring ortho ester 9 in aqueous hydrogen peroxide with a palladium catalyst, the internal olefin moiety of 9 is oxidized in greater than 90% yield, producing methyl ketone 10 in 61% yield and the ethyl ketone in approximately 30% yield (product not shown). While these conditions provided the fewest number of side products, extended reaction times were found to achieve full conversion. The incorporation of co-solvents or phase-transfer catalysts to enhance solubility resulted in increased conversion when compared to water alone.

In an effort to convert methyl ketone 10 to artemisinin (1), a number of disparate oxidative rearrangement strategies were evaluated. Higher yields were obtained by subjecting 10 to the combination of ammonium molybdate and hydrogen peroxide. Without being bound to any particular theory, it is believed that this final oxidative rearrangement utilizes the in situ formation of singlet oxygen from the decomposition of H$_2$O$_2$ by ammonium molybdate to oxidize the enol olefin moiety of 10 [28]. Again without being bound to any particular theory, it is believed that, following oxidation, several oxidized intermediates converge to artemisinin (1) with a yield of 29-42% in the presence of acid.

Experimental

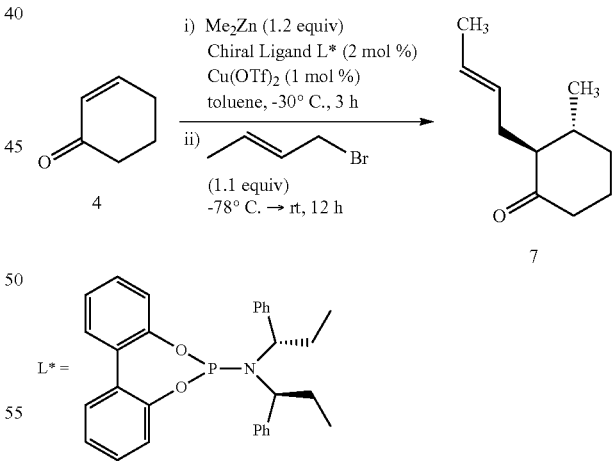

To a flame-dried flask was added Cu(OTf)$_2$ (0.94 grams (g), 2.6 millimoles (mmol)), phosphoramidite ligand L* (2.4 g, 5.2 mmol) and anhydrous toluene (500 mL) under a nitrogen atmosphere. This mixture was stirred for 30 minutes (min) at room temperature and then to which cyclohex-2-enone 4 (25 g, 260 mmol) was added. The mixture was stirred at room temperature for 20 min before cooling to −30° C., then dimethylzinc (260 mmol) was added to the solution. The reaction was stirred at −30° C. until complete consumption of starting material which was indicated by TLC (usually 3 hours (h)). Then, the above solution was cooled −78° C. before crotyl bromide (38.6 g, 286 mmol) was added. The reaction was allowed to come to room temperature over 4 hours and stirred for additional 8 hours before 300 mL saturated aqueous ammonium chloride was added at 0° C. The organic phase was separated and the aqueous phase was extracted twice with 300 mL hexanes, then the combined organics were dried over $MgSO_4$, filtered and concentrated in vacuo. The dark red crude mixture was purified by flash chromatography (hexanes/ethyl acetate, 20/1) to afford desired product 7 as pale yellow oil.

Yield 26 g, 61% and 7/1 dr. IR (film) v/cm⁻¹ 2929 (s), 2870 (m), 1711 (s), 1454 (m), 971 (m). $[\alpha]_D^{20}$=+28.1 (c 0.980, $CHCl_3$). ¹H NMR (400 MHz, $CDCl_3$) δ 5.36-5.49 (m, 2H), 2.30-2.40 (m, 2H), 2.21-2.28 (m, 2H), 2.00-2.06 (m, 1H), 1.94-1.99 (m, 1H), 1.82-1.88 (m, 1H), 1.60-1.75 (m, 5H), 1.39-1.49, (m, 1H), 1.03 (d, J=6.8 Hz, 3H). ¹³C NMR (100 MHz, $CDCl_3$) δ 212.6, 128.9, 126.4, 57.2, 41.5, 37.6, 33.2, 29.8, 25.4, 20.3, 17.9. CI-HRMS calculated for $C_{11}H_{19}O$ [M+H] 167.1430. found 167.1433.

To a stirred solution of 1.6 M n-butyllithium (n-BuLi) (392 mL, 628 mmol) was slowly added a solution of hydrazide in 300 mL tetramethylethylenediamine (TMEDA) at −78° C. over 15 minutes. Then, the reaction was warmed to room temperature and stirred at room temperature for 90 minutes before the addition of 60 mL DMF at 0° C. The resulting mixture was stirred at 0° C. for 1 hour before 300 mL saturated aqueous ammonium chloride being added at 0° C. The organic phase was separated and the aqueous phase was extracted twice with 300 mL hexanes, then the combined organics were dried over $MgSO_4$, filtered and concentrated in vacuo. The dark yellow crude mixture was purified by flash chromatography (hexanes/ethyl acetate, 10/1 eluent) to afford desired product 5b as pale yellow oil. Yield 20 g, 72% from ketone.

IR (film) v/cm⁻¹ 2957 (m), 2931 (s), 2873 (w), 1685 (s), 1639 (m), 1167 (m), 968 (m). $[\alpha]_D^{20}$=−45.2 (c 1.1, $CHCl_3$). 1H NMR (400 MHz, $CDCl_3$) δ 9.38 (s, 1H), 6.76 (d, J=3.6 Hz, 1H), 5.36-5.39 (m, 2H), 2.27-2.30 (m, 3H), 1.91-1.98 (m, 2H), 1.72-1.81 (m, 1H), 1.63-1.66 (m, 4H), 1.36-1.42 (m, 1H), 0.86 (d, J=6.8 Hz, 3H). ¹³C NMR (100 MHz, $CDCl_3$) δ 194.6, 151.4, 143.5, 129.4, 126.5, 37.8, 36.3, 27.5, 23.7, 23.0, 18.5, 17.9. CI-HRMS calculated for $C_{12}H_{19}O$ [M+H] 179.1430. found 179.1429.

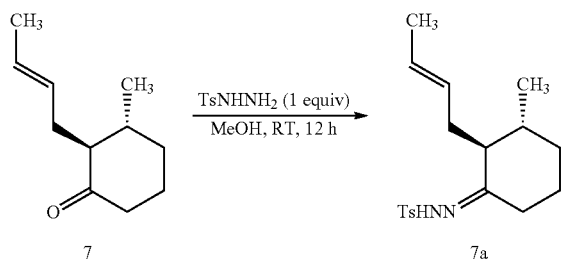

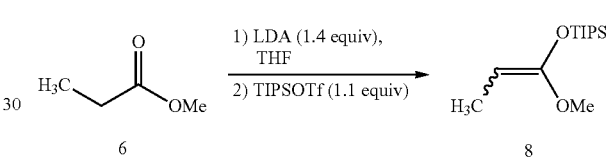

To a solution of ketone 7 (26 g, 157 mmol) in 100 mL MeOH was added $TsNHNH_2$ (29 g, 157 mmol) at 0° C. The reaction was allowed to come to room temperature over 2 hours and stirred for additional 10 hours before concentrated in vacuo. The sticky crude mixture could be used without further purification or be purified by flash chromatography (hexanes/ethyl acetate, 20/1) to afford desired product as white sticky gum.

IR (film) v/cm⁻¹ 3225 (s), 2938 (s), 1705 (m), 1599 (m), 1163 (m), 812 (m). $[\alpha]_D^{20}$=+38.9 (c 0.79, $CHCl_3$). ¹H NMR (400 MHz, $CDCl_3$) δ 7.81 (d, J=8.4 Hz, 2H), 7.72 (brs, 1H), 7.27 (d, J=8.4 Hz, 2H) 5.35-5.44 (m, 1H), 5.04-5.11 (m, 1H), 2.49-2.53 (m, 1H), 2.39 (s, 3H), 2.09-2.29 (m, 5H), 1.89-1.96 (m, 1H), 1.69-1.78 (m, 1H), 1.59-1.61 (m, 1H), 1.45 (d, J=6.4 Hz, 2H), 1.38-1.42 (m, 1H), 1.25-1.29 (m, 1H), 0.77 (d, J=7.2 Hz, 3H). ¹³C NMR (100 MHz, $CDCl_3$) δ 163.0, 143.6, 135.4, 129.3, 129.1, 128.1, 125.7, 50.6, 35.3, 32.1, 31.2, 25.6, 23.0, 21.5, 19.6, 17.7. ESI-TOF-HRMS calculated for $C_{18}H_{27}N_2O_2S$ [M+H] 357.1793. found 335.1781.

To a solution of diisopropylamine (0.75 g, 7.5 mmol) in THF (10 mL) was added 2.5 M nBuLi (2.8 mL, 7 mmol) at 0° C. The resulting mixture was stirred for 30 minutes at 0° C. before methyl propionate 6 (0.44 g, 5 mmol) was added at −78° C. After stirring at −78° C. for 90 min, TIPSOTf (1.69 g, 5.5 mmol) was added to the reaction. The reaction mixture was allowed to come to room temperature over 2 hours and then filtered through a pad of aluminum to yield a colorless solution which was concentrated in vacuo. The crude product 8 was used without further purification.

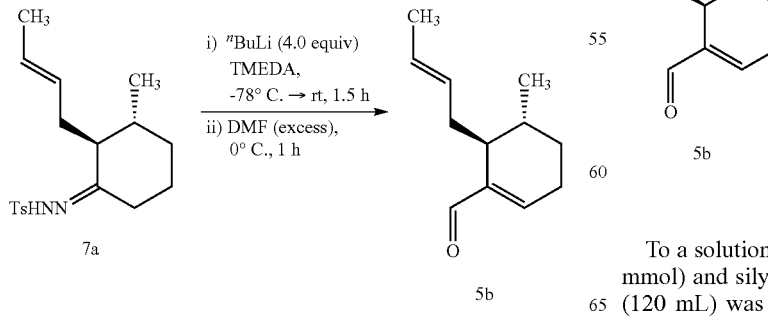

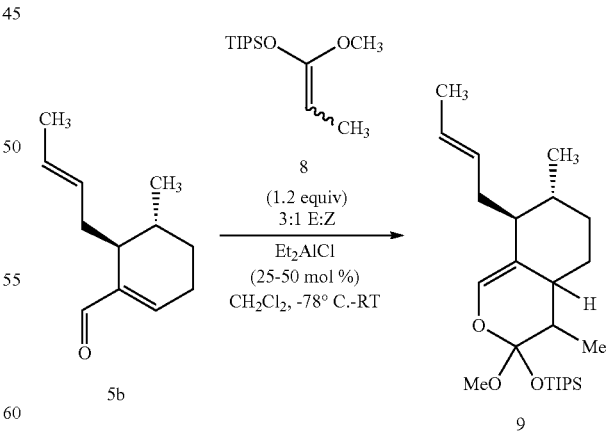

To a solution of the unsaturated aldehyde 5b (20.0 g, 113 mmol) and silyl ketene acetal 8 (33 g, 135 mmol) in DCM (120 mL) was added $Et_2AlCl$ (28 mmol) at −78° C. The reaction mixture was allowed to come to room temperature over 2 hours and then stirred at room temperature for 12 hours before 200 mL saturated aqueous ammonium chloride being added at 0° C. The organic phase was separated and the aqueous phase was extracted twice with 200 mL ethyl acetate, then the combined organics were dried over MgSO$_4$, filtered and concentrated in vacuo. The yellow crude mixture was filtered through silica (hexanes/ethyl acetate, 10/1 eluent) to afford desired product 9 as pale yellow oil. Yield: 47 g, >98%.

IR (film) v/cm$^{-1}$ 3429 (s), 2944 (s), 2867 (s), 1739 (s), 1651 (s), 1462 (m), 1159 (s), 882 (m). [α]$_D^{20}$=+45.2 (c 0.970, CHCl$_3$). $^1$H NMR (400 MHz, CDCl$_3$) δ 6.30 (s, 1H), 5.37-5.42 (m, 2H), 3.67 (s, 3H), 2.66-2.75 (m, 2H), 2.08-2.12 (m, 3H), 1.70-1.85 (m, 3H), 1.61-1.62 (m, 2H), 1.05-1.18 (m, 27H), 0.89 (d, J=7.2 Hz, 3H). $^{13}$C NMR (100 MHz, CDCl$_3$) δ 178.0, 138.2, 131.3, 125.3, 116.1, 51.4, 42.3, 41.6, 38.9, 38.2, 31.1, 24.5, 23.8, 19.5, 17.9, 17.7, 17.0, 11.9. ESI-TOF-HRMS calculated for C$_{25}$H$_{46}$O$_3$NaSi [M+Na] 445.3114. found 445.3133.

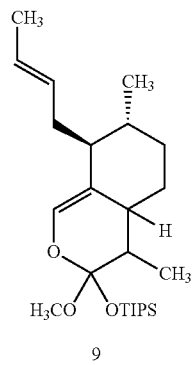

9

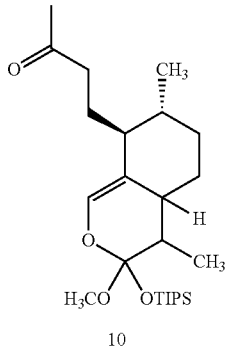

10

To a mixture of PdCl$_2$ (0.315 g, 1.8 mmol) and olefin 9 (15 g, 35 mmol) was added 35% H$_2$O$_2$ (50 mL, 15 equiv) at room temperature. Due to the heterogeneous nature of the reaction, vigorous stirring was applied. Additional H$_2$O$_2$ (1-2 equiv) was added to the reaction at once every 24 h. The reaction mixture was stirred for four days before being partitioned between ethyl acetate (200 mL) and water (100 mL). The combined organics were dried over MgSO$_4$, filtered and concentrated in vacuo to give crude mixture containing a 2:1 mixture of methyl:ethyl ketone. Desired product 10 was isolated by flash chromatography (hexanes/ethyl acetate 10/1 eluent) in 61% yield (9.4 g). The ethyl ketone was also recovered in 31% yield.

NOTE: The reaction could also be run with 50% H$_2$O$_2$. Some batches of H$_2$O$_2$ led to significantly compromised yields (~30% overall). In such cases, the addition of a catalytic amount of butylhydroxytoluene (BHT) could often overcome this issue.

IR (film) v/cm$^{-1}$ 3437 (s), 2893 (m), 2867 (s), 1738 (s), 1719 (m), 1649 (m), 1462 (m), 1159 (s), 882 (m). [α]$_D^{20}$= +59.4 (c 0.870, CHCl$_3$). 1H NMR (500 MHz, CDCl$_3$) δ 6.36 (s, 1H), 3.67 (s, 3H), 2.66-2.72 (m, 1H), 2.57-2.61 (m, 1H), 2.40-2.55 (m, 2H), 2.09-2.14 (m, 1H), 2.10 (s, 3H), 1.81-1.88 (m, 1H), 1.69-1.77 (m, 3H), 1.61-1.67 (m, 1H), 1.26-1.32 (m, 1H), 1.12-1.19 (m, 4H), 1.06-1.08 (m, 18H), 1.02 (d, J=6.5 Hz, 3H), 0.91 (d, J=7.0 Hz, 3H). $^{13}$C NMR (125 MHz, CDCl$_3$) δ 209.2, 177.9, 139.0, 115.4, 51.4, 43.2, 42.4, 41.6, 38.6, 33.1, 29.8, 29.1, 24.7, 24.2, 19.7, 17.7, 17.0, 11.9. ESI-TOF-HRMS calculated for C$_{25}$H$_{46}$O$_4$NaSi [M+Na] 461.3063. found 461.3052.

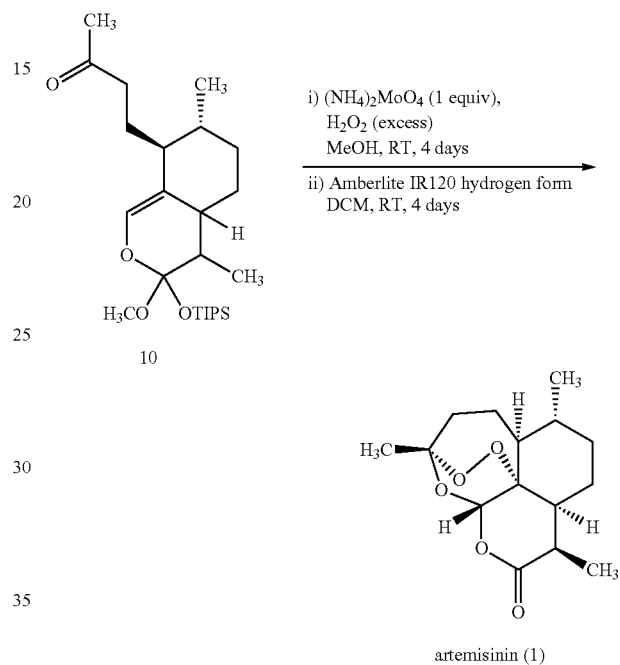

artemisinin (1)

To a solution of compound 10 (7 g, 15.4 mmol) and ammonium molybdate (1.51 g, 7.7 mmol) in t-BuOH (60 mL) was added 50% H$_2$O$_2$ (10 mL, 150 mmol). The solution was stirred with additional H$_2$O$_2$ (5 mL, 75 mmol) added every 12 hours. At 72 hours, the mixture was diluted with water (100 mL), extracted with CH$_2$Cl$_2$ (3×100 mL), dried over MgSO$_4$, filtered and concentrated. The yellow crude mixture was dissolved in DCM (50 mL) and treated with p-toluensulfonic acid (pTSA) (285 mg, 1.5 mmol). The resulting solution was stirred for 72 hours before being concentrated and filtered through a plug of silica (hexanes/diethyl ether 10:1 eluent). The resulting yellow oil could be purified by flash chromatography (ethyl acetate in hexanes 0% to 20%), or recrystallized from heptane to obtain 1.26 g artemisinin (1) (29% yield).

NOTE: Amberlite IR120 hydrogen form and other homogenous proton sources could also be used in place of p-toluenesulfonic acid.

IR (film) v/cm$^{-1}$ 2956 (m), 2933 (m), 2884 (m), 2861 (m), 1739 (s), 1201 (m), 1114 (s), 1033 (m), 1028 (m), 995 (s), 883 (m). [α]$_D^{20}$=+64.0 (c 1.20, CHCl$_3$) (nat. [α]$_D^{20}$=+66.6 (c 0.90, CHCl$_3$)). $^1$H NMR (400 MHz, CDCl$_3$) δ 5.84 (s, 1H), 3.38 (dq, J=7.4, 5.5 Hz, 1H), 2.41 (ddd, J=14.4, 12.9, 3.9 Hz, 1H), 2.06-1.92 (m, 2H), 1.90-1.82 (m, 1H), 1.79-1.70 (m, 2H), 1.52-1.31 (m, 3H), 1.42 (s, 3H), 1.18 (d, J=7.4 Hz, 3H), 1.10-1.00 (m, 2H), 0.98 (d, J=5.9 Hz, 3H). $^{13}$C NMR (100 MHz, CDCl$_3$) δ 172.7, 106.0, 94.3, 80.1, 50.7, 45.6, 38.2, 36.5, 34.2, 33.5, 25.8, 25.5, 24.0, 20.5, 13.2. HRMS calculated for $C_{15}H_{22}O_5Na$ [M+Na] 305.1365. found 305.1356.

REFERENCES

1. World Malaria Report. 248 (World Health Organization, 2011).
2. Chang, M. C., Eachus, R. A., Trieu, W., Ro, D. K. & Keasling, J. D. Engineering *Escherichia coli* for production of functionalized terpenoids using plant P450s. Nat. Chem. Biol. 3, 274-277 (2007).
3. Ro, D. K. et al. Production of the antimalarial drug precursor artemisinic acid in engineered yeast. Nature 440, 940-943 (2006).
4. Graham, I. A. et al. The genetic map of *Artemisia annua* L. identifies loci affecting yield of the antimalarial drug artemisinin. Science 327, 328-331 (2010).
5. Wender, P. A., Verma, V. A., Paxton, T. J. & Pillow, T. H. Function-oriented synthesis, step economy, and drug design. Acc. Chem. Res. 41, 40-49 (2008).
6. Liu, J.-M. et al. Structure and reaction of arteannuin. Hua. Xue. 37, 129-143 (1979).
7. Zhou, W. S. & Xu, X. X. Total Synthesis of the Antimalarial Sesquiterpene Peroxide Qinghaosu and Yingzhaosu-A. Acc. Chem. Res. 27, 211-216 (1994).
8. Schmid, G. & Hofheinz, W. Total Synthesis of Qinghaosu. J. Am. Chem. Soc. 105, 624-625 (1983).
9. Xu, X. X., Zhu, J., Huang, D. Z. & Zhou, W. S. Total Synthesis of Arteannuin and Deoxyarteannuin. Tetrahedron 42, 819-828 (1986).
10. Avery, M. A., Jenningswhite, C. & Chong, W. K. M. The Total Synthesis of (+)-Artemisinin and (+)-9-Desmethylartemisinin. Tetrahedron Lett. 28, 4629-4632 (1987).
11. Ravindranathan, T., Kumar, M. A., Menon, R. B. & Hiremath, S. V. Stereoselective synthesis of artemisinin. Tetrahedron Lett. 31, 755-758 (1990).
12. Avery, M. A., Chong, W. K. M. & Jenningswhite, C. Stereoselective Total Synthesis of (+)-Artemisinin, the Antimalarial Constituent of *Artemisia-Annua* L. J. Am. Chem. Soc. 114, 974-979 (1992).
13. Liu, H. J., Yeh, W. L. & Chew, S. Y. A Total Synthesis of the Antimalarial Natural Product (+)-Qinghaosu. Tetrahedron Lett. 34, 4435-4438 (1993).
14. Constantino, M. G., Beltrame, M. & daSilva, G. V. J. A novel asymmetric total synthesis of (+)-artemisinin. Synthetic Commun. 26, 321-329 (1996).
15. Liu, H. J. & Yeh, W. L. Total synthesis of (−)-qinghaosu IV (artemisinin D, arteannuin D). Heterocycles 42, 493-497 (1996).
16. Yadav, J. S., Thirupathaiah, B. & Srihari, P. A concise stereoselective total synthesis of (+)-artemisinin. Tetrahedron 66, 2005-2009 (2010).
17. White, N. J. Qinghaosu (artemisinin): the price of success. Science 320, 330-334 (2008).
18. Martin, V. J., Pitera, D. J., Withers, S. T., Newman, J. D. & Keasling, J. D. Engineering a mevalonate pathway in *Escherichia coli* for production of terpenoids. Nat. Biotechnol. 21, 796-802 (2003).
19. Tsuruta, H. et al. High-level production of amorpha-4,11-diene, a precursor of the antimalarial agent artemisinin, in *Escherichia coli*. Plos One 4, e4489 (2009).
20. Westfall, P. J. et al. Production of amorphadiene in yeast, and its conversion to dihydroartemisinic acid, precursor to the antimalarial agent artemisinin. Proc. Natl. Acad. Sci. U.S.A. 109, E111-118 (2012).
21. Van Noorden, R. Demand for malaria drug soars. Nature 466, 672-673 (2010).
22. Stork, G. & Jung, M. E. Vinylsilanes as Carbonyl Precursors—Use in Annelation Reactions. J. Am. Chem. Soc. 96, 3682-3684 (1974).
23. Singletary, J. A., Lam, H. & Dudley, G. B. A succinct method for preparing the Stork-Jung vinylsilane robinson annulation reagent. J. Org. Chem. 70, 739-741 (2005).
24. Jarugumilli, G. K., Zhu, C. & Cook, S. P. Re-Evaluating the Nucleophilicity of Zinc Enolates in Alkylation Reactions. Eur. J. Org. Chem. 2012, 1712-1715 (2012).
25. Shapiro, R. H., Lipton, M. F., Kolonko, K. J., Buswell, R. L. & Capuano, L. A. Tosylhydrazones and Alkyllithium Reagents—More on Regiospecificity of Reaction and Trapping of 3 Intermediates. Tetrahedron Lett. 16, 1811-1814 (1975).
26. Aben, R. W. M. & Scheeren, H. W. High Pressure-Promoted Cyclo-Additions of Ketene Acetals and Alpha,Beta-Unsaturated Aldehydes and Ketones. Tetrahedron Lett. 26, 1889-1892 (1985).
27. Hoppe, H. W., Stammen, B., Werner, U., Stein, H. & Welzel, P. An Approach to Bufadienolides from Deoxycholic-Acid—Reactions of a Steroidal Alpha,Beta-Unsaturated Aldehyde with Some Ortho-Silylated Ketene Acetals. Tetrahedron 45, 3695-3710 (1989).
28. Reiling, K. K., Renninger, N. S., McPhee, D. J., Fisher, K. J. & Ockey, D. A. Conversion of amorpha-4,11-diene to artemisinin and artemisinin precursors U.S. 2006/0270863 (2006).
29. Taber, D. F. A simple synthesis of 2-alkyl cyclohexenones. J. Org. Chem. 41: 2649, 1976.

The invention claimed is:

1. A method for manufacturing molecules of Formula F:

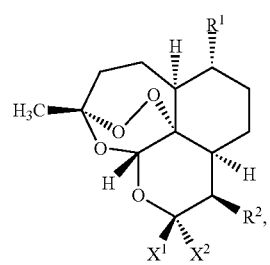

the method comprising the steps of:

reacting a first mixture comprising cyclohexenone, an alkylating agent and a methyl vinyl ketone (MVK) equivalent to form a first synthetic intermediate of Formula B:

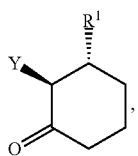

B wherein R¹ is an alkyl moiety and moiety Y is a moiety derived from the MVK equivalent and that can be converted subsequently to a —CH₂CH₂C(O)CH₃ moiety;

reacting a second mixture comprising the intermediate of Formula B and a formylating agent under basic conditions to form an aldehyde intermediate of Formula C:

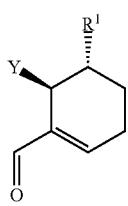

C reacting a third mixture comprising the intermediate of Formula C and a dienophile under [4+2] reaction conditions to form an intermediate of Formula D:

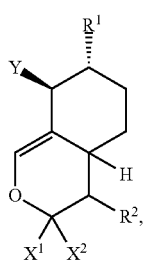

D wherein: R² is selected from the group consisting of —H, alkyl, cycloalkyl, heterocycle, and aryl, and
X¹ and X² are independently selected from the group consisting of —H, —OH, —OCH₃, —OCH₂CH₃, —OSiR', —OR", wherein R' is alkyl and R" is alkyl, or X¹ and X² together form an oxo;

reacting a fourth mixture comprising intermediate D and an MVK converting agent to form an intermediate of Formula E:

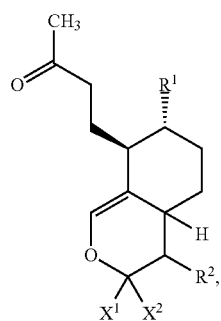

E wherein the MVK converting agent reacts with the moiety Y of compound D to convert moiety Y to a —CH₂CH₂C(O)CH₃ moiety; and reacting a fifth mixture comprising the intermediate of Formula E, hydrogen peroxide and a metal catalyst to form molecules of Formula F.

2. The method of claim 1, wherein the alkylating agent is dimethylzinc.

3. The method of claim 1, wherein the MVK equivalent is crotyl bromide.

4. The method of claim 1, wherein the second mixture further comprises a sulfonylhydrazide and the formylating agent comprises dimethylformamide.

5. The method of claim 1, wherein the dienophile is selected from the group consisting of CH₃CH₂C(O)Cl, (CH₃O)(TIPSO)CH=CHCH₃, and CH₃CH=CHOR, wherein R is selected from the group consisting of —H, —CH₃, —CH₂CH₃, and —C(O)(CH₂)₂CO₂Na.

6. The method of claim 1, wherein the third mixture further comprises a dialkylaluminum chloride.

7. The method of claim 1, wherein the MVK converting agent comprises a peroxide oxidizer and a palladium catalyst.

8. The method of claim 1, wherein the metal catalyst comprises a metal selected from the group consisting of lanthanum, cerium, molybdenum, calcium, tungsten, scandium, titanium, zirconium, vanadium, and combinations thereof.

9. The method of claim 1, wherein the metal catalyst comprises molybdenum.

10. A method for manufacturing artemisinin, comprising the steps of:

reacting a first mixture comprising cyclohexenone, a methylating agent and crotyl bromide to form a first synthetic intermediate of Formula 7:

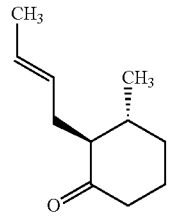

7 reacting a second mixture comprising the intermediate of Formula 7 and a formylating agent under basic conditions to form an aldehyde intermediate of Formula 5b:

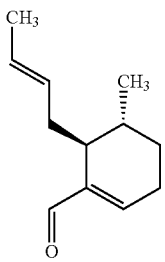

5b reacting a third mixture comprising the intermediate of Formula 5b and a compound of Formula 8 to form an intermediate of Formula 9:

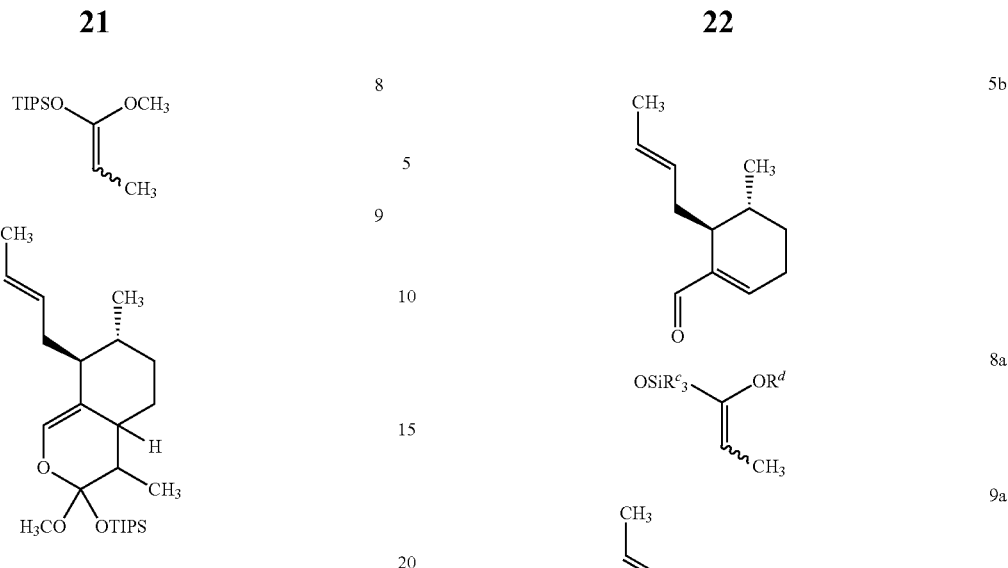

reacting a fourth mixture comprising the intermediate of Formula 9, hydrogen peroxide and a palladium catalyst to form an intermediate of Formula 10:

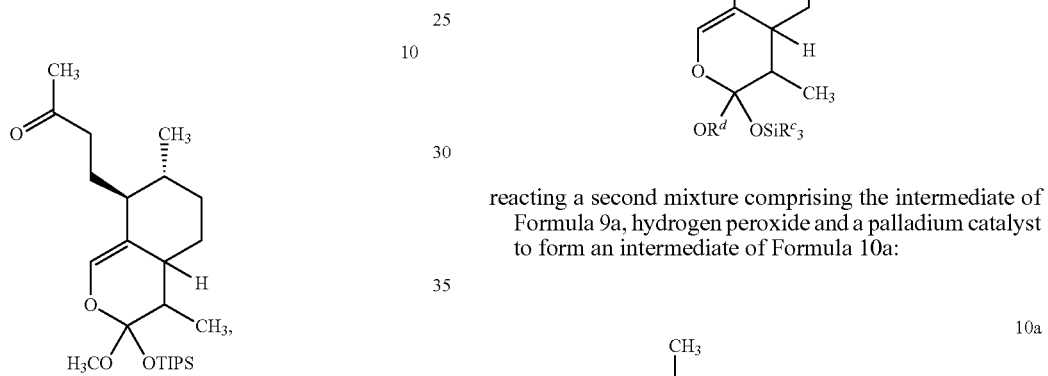

and reacting a fifth mixture comprising the intermediate of Formula 10, hydrogen peroxide and a molybdenum catalyst to form artemisinin.

11. The method of claim 10, wherein the methylating agent is dimethylzinc.

12. The method of claim 10, wherein the second mixture further comprises a sulfonylhydrazide and the formylating agent comprises dimethylformamide.

13. The method of claim 10, wherein the third mixture further comprises a dialkylaluminum chloride.

14. The method of claim 13, wherein the dialkylaluminum chloride is diethylaluminum chloride.

15. The method of claim 10, wherein the palladium catalyst is palladium chloride.

16. The method of claim 10, wherein the molybdenum catalyst is $(NH_4)_2MoO_4$.

17. A method for manufacturing artemisinin, comprising the steps of:

reacting a first mixture comprising a compound of Formula 5b and a compound of Formula 8a under [4+2] reaction conditions to form an intermediate of Formula 9a:

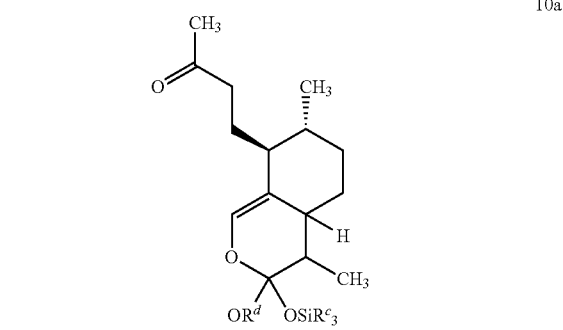

reacting a second mixture comprising the intermediate of Formula 9a, hydrogen peroxide and a palladium catalyst to form an intermediate of Formula 10a:

10a

[structure 10a]

and reacting a third mixture comprising the intermediate of Formula 10a, hydrogen peroxide and a catalyst comprising molybdenum, wherein $R^c$ is alkyl and $R^d$ is alkyl, to form artemisinin.

18. The method of claim 17, wherein the catalyst comprising molybdenum is a molybdenum salt.

19. The method of claim 17, wherein the catalyst comprising molybdenum is $(NH_4)_2MoO_4$.

20. The method of claim 17, wherein $R^c$ is an $—CH(CH_3)_2$ moiety and $R^d$ is a $—CH_3$ moiety.

* * * * *